(12) United States Patent
Minomi et al.

(10) Patent No.: US 7,521,415 B2
(45) Date of Patent: Apr. 21, 2009

(54) METHODS OF INTRACELLULAR PEPTIDE DELIVERY

(75) Inventors: Kenjiro Minomi, Osaka (JP); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 11/251,956

(22) Filed: Oct. 17, 2005

(65) Prior Publication Data

US 2006/0083737 A1     Apr. 20, 2006

Related U.S. Application Data

(60) Provisional application No. 60/619,729, filed on Oct. 18, 2004.

(51) Int. Cl.
*A61K 38/04* (2006.01)
*A61K 38/02* (2006.01)
*A61K 38/00* (2006.01)

(52) U.S. Cl. .................. 514/2; 514/12; 514/13; 514/14; 514/15; 514/16; 514/17

(58) Field of Classification Search .............. None
See application file for complete search history.

(56) References Cited

U.S. PATENT DOCUMENTS

| | | | |
|---|---|---|---|
| 7,048,925 | B2 | 5/2006 | Van et al. |
| 7,163,677 | B2 | 1/2007 | Li et al. |
| 7,220,414 | B2 * | 5/2007 | Brocchini et al. ........ 424/181.1 |
| 7,348,453 | B2 * | 3/2008 | Rozema et al. ............ 562/473 |
| 2004/0115135 | A1 * | 6/2004 | Quay .......................... 424/46 |
| 2004/0166089 | A1 | 8/2004 | Yu et al. |
| 2005/0191746 | A1 * | 9/2005 | Van et al. ................... 435/455 |

OTHER PUBLICATIONS

Ogris et al. (2001) AAPA PharmSci, vol. 3, p. 1-11.*
Qbiogene, Overview of jetPEI™ Transfection Technology.*
Definition of heterologous -Merriam-Webster Online Dictionary.*
SuperFect® (Dec. 2002, see SuperFect® Transfection Reagent Handbook from Qiagen).*
Dodds et al. (1999) J. Neuroche, vol. 72, p. 2105-2112.*
Stayton et al. (2001) Bioinspired nanocarriers designed to enhance intracellular delivery of biotherapeutics, Engineering in Medicine and Biology Society, 2001. Proceedings of the 23rd Annual International Conference of the IEEE, vol. 4 pp. 4092-4093.*
Murthy et al. (2003) Bioinspired pH-responsive polymers for the intracellular delivery of biomolecular drugs, Bioconjug. Chem., vol. 14, No. 2, pp. 412-419.*
Kitazoe et al. (2005) Protein transduction assisted by polyethylenimine-cationized carrier proteins, J. Biochem., vol. 137, No. 66, pp. 693-701.*
Dalkara, et al. "Intracytoplasmic Delivery of Anionic Proteins," *Molecular Therapy*, vol. 9, No. 6, pp. 964-969, Jun. 2004.
Futaki, et al. "Arginine-Rich Peptides, An Abundant Source of Membrane-Permeable Peptides Having Potential as Carriers for Intracellular Protein Delivery," *The Journal of Biological Chemistry*, vol. 276, No. 8, pp. 5836-5840, Feb. 23, 2001.
Hui, et al. "The Role of Helper Lipids in Cationic Liposome-Mediated Gene Transfer," *Biophysical Journal*, vol. 71, pp. 590-599, Aug. 1996.
Padilla, et al. Pretreatment with Polycations Enhances Adenoviral Infection Levels in Serum-Free PER.C6™ Cells as Well as HRK 293 Cells,P May 2003, pp. 1-2, XP002368720 Retriefed from the Internet: URL: http://www.jrhbio.com/Document.aspx?ID=610>.
Suzuki, et al. Possible Existence of Common Internalization Mechanisms Among Arginine-Rich Peptides, *The Journal of Biological Chemistry*, vol. 277, No. 4, pp. 2437-2443, Jan. 25, 2002.
Vancha, et al. "Use of Polyethyleneimine Polymer in Cell Culture as Attachment Factor and Lipofection Enhancer," *BMC Biotechnology*, vol. 4, No. 23, pp. 1-12, Oct. 15, 2004.
International Search Report completed Feb. 23, 2006.

* cited by examiner

*Primary Examiner*—Jon P Weber
*Assistant Examiner*—Samuel W Liu
(74) *Attorney, Agent, or Firm*—Knobbe, Martens, Olson & Bear, LLP

(57) ABSTRACT

Methods and kits for transporting heterologous compounds into cells, particularly mammalian cells, are disclosed. The method involves the pretreatment of the cell with a polycation, cationic polymer and/or cationic peptide before transportation of the heterologous compound into the cell. The methods are particularly applicable to the transport of peptides and proteins.

12 Claims, 9 Drawing Sheets

Control
FIG. 1A

Biotin-Tat
FIG. 1B

Biotin-Tat + jet-PEI
FIG. 1C

Biotin-Tat + SuperFect
FIG. 1D

FIG. 2A Control

1mM Tat FIG. 2B

10mM Tat FIG. 2C jet-PEI FIG. 2D

SuperFect FIG. 2E

FIG. 3B
jet-PEI® (Pretreatment)

FIG. 3E
SuperFect® (Pretreatment)

FIG. 3C
jet-PEI® (Simultaneous)

FIG. 3F
SuperFect® (Simultaneous)

FIG. 3A
No Peptide

FIG. 3D
Control

FIG. 4A PEI (MW. 25,000)

FIG. 4B PEI (MW. 10,000)

FIG. 4C PEI (MW. 1,800)

FIG. 4D PEI (MW. 1,200)

FIG. 4E PEI (MW. 600)

FIG. 4F Control

Control
FIG. 5A

NDT #2
FIG. 5B

NDT #5
FIG. 5C

NDT-PA-PEI-1,200
FIG. 5F

NDT-PA-PEI-1,800
FIG. 5G

R7C
FIG. 6B

SuperFect®
FIG. 6D

No Enhancer
FIG. 6A jet-PEI®
FIG. 6C

FIG. 7A
+ beta-galactosidase

FIG. 7B
- beta-galactosidase

FIG. 7C
R7C

FIG. 7D
jet-PEI®

FIG. 7E
SuperFect®

FIG. 8A

PA-PEI₁₈₀₀ where molecular weight of PEI is 1800 daltons,
PA-PEI₁₂₀₀ where molecular weight of PEI is 1200 daltons,

FIG. 8B

METHODS OF INTRACELLULAR PEPTIDE DELIVERY

RELATED APPLICATIONS

This application claims priority to U.S. Provisional Application No. 60/619,729, filed Oct. 18, 2004 and incorporated herein by reference.

BACKGROUND OF THE INVENTION

1. Field of the Invention

This invention relates to transport of compounds into cells, in particular, transport of heterologous compounds such as peptides and proteins, into eukaryotic cells.

2. Description of the Related Art

The plasma membranes of cells present a barrier to passage of many useful therapeutic agents. In general, a molecule must be freely soluble in both the aqueous compartments of the body and the lipid layers through which it must pass, in order to enter cells. Many therapeutic macromolecules such as peptides and oligonucleotides are also particularly intractable to transmembrane transport. Current DNA transfection techniques include microinjection, calcium phosphate co-precipitation, cationic liposomes, viral vectors and electroporation. These methods are capable of transporting DNA into cells, but the techniques are cumbersome and cytotoxic. Furthermore, once transfection has been completed, the researcher must wait 12-80 h after transfection to detect expression of the gene of interest.

Recently, novel methods have been developed for the delivery of exogenous peptides and proteins directly into living cells with the help of protein transduction domains such as HIV-1 Tat (48-60) (A. Frankel and C. Pabo, Cellular uptake of the Tat protein from human immunodeficiency virus. Cell 55 (1988), pp. 1189-1193; M. Green and P. Loewenstein, Autonomous functional domains of chemically synthesized human immunodeficiency virus Tat trans-activator protein. Cell 55 (1988), pp. 1179-1188). However, this method has drawbacks. Protein transduction via Tat-fusion proteins resulted in inactivation and denaturation of the cargo protein. To deliver an active protein, correct renaturation is required upon internalization. In addition, Tat must be covalently linked by a chemical reaction to the compounds or macromolecules to be delivered.

Another transduction domain protein has been reported from the *Drosophila Antennapedia* homeotic transcription factor (43-58) (A. Joliot, A. Triller, M. Volovitch, C. Pemelle and A. Prochiantz, Alpha-2-8-polysialic acid is the neuronal surface receptor of antennapedia homeobox peptide. New Biol 3 (1991), pp. 1121-1134.; I. Le Roux, A. H. Joliot, E. Bloch-Gallego, A. Prochiantz and M. Volovitch, Neurotrophic activity of the antennapedia homeodomain depends on its specific DNA-binding properties. Proc Natl Acad Sci USA 90 (1993), pp. 9120-9124). A commercially available protein transduction domain peptide, PENETRATIN® (U.S. Pat. No. 5,888,762) based upon this peptide consists of 16 amino acids corresponding to the third helix of the homeodomain of antennapedia protein. Activated PENETRATIN® has an N-terminal pyridyl disulfide that covalently couples with cargo peptides. However, chemical coupling is potentially cumbersome and cargo peptides must have a free thiol group for chemical coupling with this reagent.

Another protein transduction domain peptide utilizes the translocation properties of the 38 kDa herpes simplex virus-1 DNA binding protein, VP22 (G. Elliott and P. O'Hare, Intercellular trafficking and protein delivery by a herpes virus structural protein. Cell 88 (1997), pp. 223-233). However, VP22 must be fused to the peptide/protein to be delivered and requires the construction of a suitable expression vector to make the fusion protein.

Rothbard, et al. (U.S. Pat. No. 6,306,993) disclose a method for enhancing transport of a compound across a biological membrane, by conjugation between the transported compound and a transport polymer by covalent attachment. The transport polymer includes subunits, at least 50% of which contain a guanidino or amidino sidechain moiety. U.S. Pat. No. 6,306,993 also requires a covalent attachment of the cargo molecule to the transporter.

For the carrier peptides described above, hybridization of the carrier peptides either genetically or chemically with the molecule to be transported was required for the efficient intracellular delivery of the various cargo peptides and proteins.

WO02/10201 (Divida, et al.) disclose a transfection agent that includes a peptide (15-30 residues) with hydrophobic and hydrophilic domain which provides a non-covalent association with and transport of a heterologous compound into a cell. This agent is commercially available as, CHARIOT™, which delivers biologically active proteins, peptides and antibodies directly into cultured mammalian cells at an efficiency of 60-95%. The CHARIOT™ peptide forms a non-covalent bond with cargo peptides. This may stabilize the protein, protect the cargo protein from degradation and preserve the natural characteristics of the cargo protein during the transfection process. Although covalent attachment is not required, it is necessary to prepare a mixture of CHARIOT™ and the cargo peptides before delivery.

Generally, in order to successfully deliver peptides into desired cells, the protein transduction domains, Tat, VP22 and antennapedia protein, require covalent linkage to the cargo compounds or macromolecules by either chemical reaction or a biological process such as preparation of a recombinant fusion protein. The preparation of the covalently linked cargo peptide is potentially complex, labor-intensive, and time consuming. The preparation of the cargo protein for transport by such methods also inactivates the biological function(s) of the cargo peptide. While the commercially available protein transduction domain peptide, CHARIOT™, does not require a covalent attachment, it is necessary to make a mixture of CHARIOT™ and the cargo peptides before applying to the cells. This mixing time is also potentially time consuming.

SUMMARY OF THE INVENTION

Some embodiments of the invention are directed to a method of transporting a heterologous compound into a cell which includes the steps of pretreating the cell with a composition which includes at least one compound which is a polycation, a cationic polymer or a cationic peptide; and transporting the heterologous compound into the pretreated cell.

In some preferred embodiments, the cationic polymer is a polyethyleneimine derivative. Preferably, the polyethyleneimine derivative is biodegradable. More preferably, the polyethyleneimine derivative is pH-sensitive degradable. In some preferred embodiments, the polyethyleneimine derivative is conjugated with a lipid.

In some preferred embodiments, the composition for pretreating the cell includes a cationic peptide. In a preferred embodiment, the cationic peptide is HIV-Tat. In an alternate preferred embodiment, the cationic peptide is poly-arginine.

In preferred embodiments, the heterologous compound is a peptide derivative. In some preferred embodiments, the heterologous compound is a protein. In some preferred embodiments, the heterologous compound is an enzyme. In some preferred embodiments, the heterologous compound is an antibody.

In preferred embodiments, the cell into which the heterologous compound is transported is a mammalian cell. In other preferred embodiments, the cell is a reptilian cell. In other preferred embodiments, the cell is an insect cell. In preferred embodiments, the cell is an oocyte.

Some preferred embodiments of the invention are directed to a kit which includes at least one cell treated with a composition having at least one compound which is a polycation, a cationic polymer or a cationic peptide. In some preferred embodiments, the cationic polymer is a polyethyleneimine derivative. Preferably, the polyethyleneimine derivative is biodegradable. More preferably, the polyethyleneimine derivative is pH-sensitive degradable. In some preferred embodiments, the polyethyleneimine derivative is conjugated with a lipid.

In some preferred embodiments, the composition for cell treatment includes a cationic peptide. In preferred embodiments, the cationic peptide is HIV-Tat. In alternate preferred embodiments, the cationic peptide is poly-arginine.

In preferred embodiments, the cell into which the heterologous compound is to be transported is a mammalian cell. In some preferred embodiments, the cell is a reptilian cell. In some preferred embodiments, the cell is an insect cell. In some preferred embodiments, the cell is an oocyte.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 5 shows the effect of various cationic polymers on peptide delivery to HeLa cells.

FIG. 7 shows the transport of β-galactosidase into HeLa cells using poly-arginine R7C (RRRRRRRC) (SEQ ID NO: 1; FIG. 7C), jet-PEI® (Qbiogene) (FIG. 7D) and SuperFect® (Qiagen)(FIG. 7E).

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Preferred embodiments of the invention relate to the transport of heterologous compounds into cells across a biological membrane. The term "biological membrane" as used herein refers to a lipid-containing barrier which separates cells or groups of cells from the extracellular space. Biological membranes include, but are not limited to, plasma membranes, cell walls, intracellular organelle membranes, such as the mitochondrial membrane, nuclear membranes, and the like.

Heterologous compounds may include compounds which are not native to the cell being transported as well as compounds that may be found normally in the cell type into which the heterologous compound is transported. In preferred embodiments of the invention, the heterologous compound is a peptide, polypeptide, or protein or an analog thereof. In some embodiments, the protein or polypeptide may be an antigen or antibody. However, other types of compounds may also be transported into cells by the methods described herein. For example, heterologous compounds may include, but are not limited to metal ions, which are typically delivered as metal chelates; small organic molecules, and other macromolecules such as nucleic acids, and analogs thereof. In some embodiments, the heterologous compound is a peptide nucleic acid (PNA).

The term "cargo" is used to refer to the heterologous molecule that is transported into the cell.

The term "macromolecule" as used herein refers to large molecules (MW greater than 1000 daltons) exemplified by, but not limited to, peptides, proteins, oligonucleotides and polynucleotides of biological or synthetic origin. "Small organic molecule" refers to a carbon-containing agent having a molecular weight (MW) of less than or equal to 1000 daltons.

The term "peptide" as used herein refers to a compound made up of a single chain of D- or L-amino acids or a mixture of D- and L-amino acids joined by peptide bonds. Generally, peptides contain at least two amino acid residues and are less than about 50 amino acids in length.

The term "protein" as used herein refers to a compound that is composed of linearly arranged amino acids linked by peptide bonds, but in contrast to peptides, has a well-defined conformation. Proteins, as opposed to peptides, generally consist of chains of 50 or more amino acids.

The term "polypeptide" as used herein refers to a polymer of at least two amino acid residues and which contains one or more peptide bonds. "Polypeptide" encompasses peptides and proteins, regardless of whether the polypeptide has a well-defined conformation.

The term "polycation" refers to a macromolecule with many positively charged groups at physiological pH. The macromolecule may be a protein, peptide or polymer.

The term "cells" refers to both in vitro and in vivo cells. The methods described herein may be used to transport compounds to cells both in vitro and in vivo. For example, the cargo compound may be transported to cells in situ that are within a larger organism. In some embodiments, the cells may be transported in vitro and then transported to a tissue or organism in vivo.

The term "transportation agent" as used herein refers to an agent that facilitates delivery of a macromolecule to a cell. In preferred embodiments, the macromolecule is a peptide or protein and the cell is a mammalian cell. The transportation reagents are generally cations or polycations such as poly(lysine), poly(arginine), polyacetal, and polyethyleneimine (PEI). The transportation agents may be non-degradable such as poly(lysine) or degradable. Acid-sensitive polymers containing acetal linkages (polyacetals) may also be used which are more stable at physiological pH.

Methods of synthesizing degradable polymers is taught in U.S. application Ser. No. 10/692,573, filed Oct. 24, 2003 and Ser. No. 10/651,394, filed Aug. 28, 2003. Both applications are incorporated herein by reference. Briefly, a cationic polymer with degradable crosslink includes a cationic recurring unit and a crosslinking unit. The term "cationic recurring unit" is used herein in its usual sense to refer to various positively charged chemical groups incorporated into, or suitable for incorporation into, the synthetic polymer, e.g., in the polymer backbone or in a sidechain. Preferred cationic recurring units comprise an amine group that is positively charged. Positively charged amine groups include primary, secondary and tertiary amines that are positively charged under acidic conditions, as well as quaternary amines that are positively charged over a broad pH range. Most preferably, cationic recurring units comprise a quaternary amine group. Poly(amidoamine) dendrimer, polyethylenimine, and polypropylenimine are non-limiting examples of preferred synthetic polymers comprising a cationic recurring unit.

Cationic recurring units may be incorporated into the polymer by polymerization of the corresponding cationic monomers or by post-reaction. Polymerization may be copolymerization and may proceed by various polymerization mechanisms, using techniques generally known to those skilled in the art, including step and chain polymerization mechanisms, see G. Odian, Principles of Polymerization 3$^{rd}$ Ed., John Wiley (1991). Non-limiting examples of preferred cationic monomers suitable for polymerization include spermine, spermidine, pentaethylenehexamine, N-(2-aminoethyl)-1,3-propanediamine, N-(3-aminopropyl)-1,3-propanediamine, tris(2-aminoethyl)amine, N,N'-bis(2-aminoethyl)-1,3-propanediamine, N,N'-bis(2-aminopropyl)ethylenediamine, N,N'-bis(2-aminopropyl)-1,3-propanediamine, 1-(2-aminoethyl)piperazine, 1,4-bis(3-aminopropyl)piperazine, and poly(amidoamine)dendrimer. Cationic monomers may be obtained commercially or synthesized by methods known to those skilled in the art.

Crosslinked polymers contain polymer chains that are attached to one another at points other than their ends, see G. Odian, Principles of Polymerization 3$^{rd}$ Ed., John Wiley (1991). As used herein, the term "crosslinking unit" refers to a chemical group that forms part or all of the attachment point between the two chains. Thus, a crosslinking unit is attached to two or more polymer chains at a location other than the ends of the chains. Crosslinking units may be incorporated into the polymer chain by forming the polymer in the presence of a suitable crosslinking agent or by reacting polymers with one another to form attachment points.

The crosslinking unit preferably comprises at least a first degradable unit selected from the group consisting of acetal, imine and hydrazone, and at least a second degradable unit selected from the group consisting of ester, phosphoester, amide, anhydride and urethane. The first degradable unit is preferably acid-labile, and the second degradable unit is preferably hydrolyzable. Preferred crosslinking agents typically include polymerizable groups suitable for reacting with the monomers to result in attachment of the resulting polymer and crosslinking unit to one another. Preferred crosslinking agents may also include the first and second degradable units described above, or the degradable units may be formed by post-reacting the crosslinking unit formed by incorporation of the crosslinking agent into the polymer. Preferred crosslinking agents are represented by the formula $R^1_x$—(—X—$R^3$—Y—)$_z$—$R^2_y$, where $R^1$ and $R^2$ are polymerizable groups, $R^3$ is a linking group, X is a first degradable unit selected from the group of acetal, imine and hydrazone, Y is a second degradable unit selected from the group consisting of ester, phosphoester, amide, anhydride, and urethane, x and y are integers in the range of 1-3, and z is an integer in the range of 1 to 5. Preferably, $R^1$ and $R^2$ are each independently selected from the group consisting of acrylate, methacrylate, acrylamide, isothiocyanate, isocyanate, epoxide, aldehyde, acyl chloride, sulfonyl chloride, anhydride, maleimide, carboxylic acid, carboxylic acid ester, hydroxyl, amine, and amide. Preferably, $R^3$ is selected from the group consisting of aryl having from 6 to 10 carbons, cycloalkyl having from 4 to 10 carbons, —$(CH_2)_n$—, —$(CH_2O)_n$—, and —$(CH_2CH_2O)_n$—, where n is in the range of 1 to about 100, more preferably in the range of 1 to about 5. Crosslinking agents may be obtained from commercial sources or synthesized by methods known to those skilled in the art, depending on the nature of the groups to be included, e.g., polymerizable groups, first degradable group and second degradable group.

Synthetic polymers comprising a cationic recurring unit and a crosslinking unit are preferably prepared by polymerizing a cationic monomer in the presence of a crosslinking agent. Various polymerization methods may be used, depending on the nature of the polymerizable groups in the monomer and crosslinking agent. In a preferred embodiment, the cationic monomer is an aliphatic, alicyclic or aromatic hydrocarbon bearing two or more active hydrogens such that the monomer is capable of reacting with a suitable crosslinking agent.

Polymerization of cationic monomers in the presence of a crosslinking agent is preferably carried out in a suitable solvent or suspending medium. The proportions of cationic monomer and crosslinking agent are not critical and may be determined by routine experimentation. For polyamine monomers, the reactant ratio (expressed as the number of amine-reactive functional group equivalents in the cross-linking agent to the number of amine hydrogen equivalents in polyamine monomer) is preferably in the range of from about 1:10 to about 1:1. More preferably, a reactant ratio in the range of from about 1:5 to about 4:5 is employed. For crosslinking agents represented by the formula $R^1_x$—(—X—$R^3$—Y—)$_z$—$R^2_y$, the number of amine-reactive functional group equivalents is equal to x+y. For polyamines the number of amine hydrogen equivalents is the number of reactive hydrogen atoms bonded to the nitrogen atoms.

In preferred embodiments, the polymer is a polyacetal. Polyacetals are polymers that contain acetal (—O—CHR—O—) recurring units. Preferably, R is methyl. Preferred polyacetals comprise a recurring units represented by a formula selected from the group consisting of formula (I) and (II):

In formulae (I) and (II), A represents a linker group that comprises at least one acetal group; B is selected from the group consisting of —CH—, —CH(CH$_3$)—, CH$_2$CH—, —CH$_2$C(CH$_3$)—, —CH(CH$_3$)CH—, and —CHCH(CH$_3$) CH(CH$_3$)—; Z is selected from the group consisting of C(O) OR$^1$, C(O)SR$^1$, C(O)NR$^1$R$^2$, and VU; V is a linker group; U is selected from the group consisting of poly(ethyleneimine) (PEI), poly(propyleneimine) (PPI), poly(lysine), PAMAM dendrimer, octaamine dendrimer, hexadecaamine dendrimer, enhancer, and targeting receptor; R, R$^1$ and R$^2$ are each individually selected from the group consisting of hydrogen, C$_1$ to C$_{10}$ alkyl, and C$_6$ to C$_{10}$ aryl; D is a linkage selected from the group consisting of carboxylic amide, carboxylic ester, urea, and urethane; and G is selected from the group consisting of C$_4$ to C$_{20}$ alkyl, C$_6$-C$_{10}$ aryl, and —(OCH$_2$CH$_2$)$_n$—, where n is in the range of 1 to about 250. In this context, a "linker group" is a bifunctional chemical group that joins one chemical group to another. Linker groups can contain a single bifunctional chemical group such as amide, or may contain two chemical groups such as amide-amide, amide-alkyl, alkyl-amide, amine-amide, or thioether-amide. Examples of preferred linker groups include —C(O)NH—, —C(O)NH—R$^9$—C(O)NH—, —C(O)NH—R$^9$—, —R$^9$—C(O)NH—, —NH—R$^9$—C(O)NH—, —S—R$^9$—C(O)NH, where R$^9$ is selected from the group consisting of hydrogen, C$_1$ to C$_{10}$ alkyl, and C$_6$ to C$_{10}$ aryl. Examples of linker groups that comprise at least one acetal group include —OCH(CH$_3$)O—, —OCH(CH$_3$)OCH(CH$_3$)O—, —OCH(CH$_3$)O—CH$_2$CH$_2$—OCH(CH$_3$)O—, —OCH(CH$_3$)O—CH$_2$CH$_2$CH$_2$CH$_2$—OCH(CH$_3$)O—, —OCH(CH$_3$)O—CH$_2$CH$_2$OCH$_2$CH$_2$—OCH(CH$_3$)O—, and —OCH(CH$_3$)O—CH$_2$CH$_2$OCH$_2$CH$_2$OCH$_2$CH$_2$—OCH(CH$_3$)O—.

Regarding U in formulae (I) and (II), PEI and PPI, if used, preferably have a molecular weight in the range of about 200 to about 100,000 Daltons. Poly(lysine), if used, preferably has a molecular weight in the range of about 200 to about 50,000 Daltons. Molecular weights of polymers referred to herein are weight average molecular weights as measured by high performance size exclusion chromatography (light scattering detector).

In this context, an "enhancer" is a functional group that is capable of enhancing the efficiency of peptide or protein delivery to a eukaryotic cell and a "targeting receptor" is a functional group that is capable of recognizing specific receptors on a cell surface. The foregoing definitions are not mutually exclusive, and thus U may be both an enhancer and a targeting receptor. Preferably, U is selected from the group consisting of lipid, cholesterol, transferrin, antibody, antibody fragment, galactose, mannose, lipoprotein, lysosomotrophic agent, and fusogenic agent. Enhancers and targeting receptors may be attached to polyacetals in various ways, e.g., by covalent bonding to the polyacetal via a linker group V, or by conjugating an enhancer and/or a targeting receptor to Z, or both. Thus, two or more enhancers and/or targeting receptors may be attached to a polyacetal.

Polyacetals may be copolymers and thus may contain two or more different recurring units represented by the formulas (I) and/or (II), and/or other recurring units. Terms such as "polyacetal of the formula (I)", "polyacetal of the formula (II)", "polymer of the formula (I)", and "polymer of the formula (II)" thus include copolymers as well as homopolymers consisting essentially of recurring units of the formula (I) or (II).

Various methods may be used to make polyacetals. A preferred method comprises reacting a monomer represented by a formula selected from the group consisting of formula (III) and formula (IV) with a comonomer having a formula represented by formula (V):

In formulae (III), (IV) and (V), A, B, Z and G have the same meanings as set forth above, E is a reactive end group preferably selected from the group consisting of —OH, —NH$_2$, and —NH(CH$_3$); and C is a reactive end group preferably selected from the group consisting of isocyanate, NHS-ester, carboxylic acid, carboxylic ester, carboxylic acid chloride and anhydride. The polymerization reaction conditions are adjusted in a manner generally known to those skilled in the art, depending on the nature of the reactive end groups E and C. See G. Odian, Principles of Polymerization 3$^{rd}$ Ed. (1991). Optionally, the polymerization may be conducted in the presence of one or more additional comonomers having compatible reactive end groups. Preferably, the mole ratio of monomers (III) and/or (IV) to comonomer (V) in the mixture is approximately 1:1, although the exact ratio may be varied to adjust the molecular weight of the resulting polymer and/or to compensate for the presence of additional comonomers. Higher molecular weights are generally achieved when the ratio is closer to 1:1. Lower molecular weights may be achieved by using a slight excess of either the monomers (III)/(IV) or comonomer (V), and/or by including small amounts of monofunctional reactants. Preferably, the molecular weights of the resulting polyacetals (e.g., a polymer or copolymer comprising a recurring unit represented by the formulae (I) and/or (II)) are about 1,000 Daltons or greater, more preferably in the range of about 1,000 to about 250,000 Daltons.

Recurring units represented by the formulae (I) and (II) encompass two genera, one in which Z is selected from the group consisting of C(O)OR$^1$, C(O)SR$^1$, and C(O)NR$^1$R$^2$, and the other in which Z is VU. Polyacetals in which Z is selected from the group consisting of C(O)OR$^1$, C(O)SR$^1$, and C(O)NR$^1$R$^2$ are useful for making polyacetals in which Z is VU. For example, polyacetals comprising a recurring unit of the formula (I) in which Z is VU and V is —C(O)NH— are preferably made by reacting a compound represented by the formula H$_2$NU with a polyacetal comprising a recurring unit of the formula (I) in which Z is C(O)OR$^1$, as shown in formulae (VII) and (VIII):

In formulae (VII) and (VIII), U, A, B, D and G have the same meanings as set forth above, and $R^3$, $R^4$ and $R^5$ are each individually selected from the group consisting of hydrogen, $C_1$ to $C_{10}$ alkyl, and $C_6$ to $C_{10}$ aryl. For the compound represented by the formula $H_2NU$, U has the same meaning as set forth above. The reaction of the compound represented by the formula $H_2NU$ with the polyacetal of the formula (VII) or (VIII) is preferably conducted in a polar solvent such as dimethylformamide. The polyacetals of the formulae (VII) and (VIII) may be prepared by reacting corresponding monomers of the formulae (III), (IV) and (V) as described above. A "polyacetal of the formula (VII)", "polyacetal of the formula (VIII)", "polymer of the formula (VII)", or "polymer of the formula (VIII)", as those terms are used herein, includes copolymers comprising a recurring unit of the formula (VII) and/or (VIII) as well as homopolymers consisting essentially of recurring units of the formula (VII) or (VIII).

Examples of preferred polyacetals include those comprising a recurring unit that is represented by a formula selected from the group consisting of formula (IX) and formula (X):

In formulae (IX) and (X), Z has the same meaning as described above; $R^6$, $R^7$ and $R_8$ are each individually selected from the group consisting of H and —$CH_3$; X is selected from the group consisting of —$CH_2CH_2$—, —$CH_2CH_2CH_2CH_2$—, —$CH_2CH_2OCH_2CH_2$—, and —$CH_2CH_2OCH_2CH_2OCH_2CH_2$—; and Y is selected from the group consisting of linear or branched $C_4H_8$, $C_5H_{10}$, $C_6H_{12}$, $C_7H_{14}$, $C_8H_{16}$, $C_{10}H_{20}$, and $C_{12}H_{24}$. Z is prefereably VU, V is preferably C(O)NH—, and U is preferably poly(ethyleneimine), poly(lysine), an enhancer, or a targeting receptor. The poly(ethylenimine) preferably has a molecular weight in the range of about 200 to about 100,000 Daltons; the poly(lysine) preferably has a molecular weight in the range of about 200 to about 50,000 Daltons. Non-limiting examples of preferred enhancers include those selected from the group consisting of lipid, cholesterol, lipoprotein, fatty acid, lysosomotrophic agent, and fusogenic agent. Non-limiting examples of preferred targeting receptors include those selected from the group consisting of transferrin, antibody, antibody fragment, galactose, and mannose.

Polyacetals comprising recurring units of the formulae (IX) and (X) may be prepared in the same general manner as described above for the preparation of polyacetals comprising recurring units of the formulae (I) and (II) as described above. For example, a preferred embodiment provides a method comprising reacting a monomer represented by a formula selected from the group consisting of formula (XI) and formula (XII) with a comonomer represented by the formula (XIII), in which X, Y and Z have the same meanings as for the recurring units of the formulae (IX) and (X) described above:

Polyacetals comprising recurring units of the formulae (IX) and (X) may also be prepared by reacting a compound of the formula $H_2NU$ with a polymer comprising a recurring unit represented by a formula selected from the group consisting of formula (XIV) and formula (XV), in which X and Y have the same meanings as for the recurring units of the formulae (IX) and (X) described above:

(XV)

Another preferred embodiment provides a monomer represented by the formula (XI). A preferred method for making such monomers comprises reacting a divinyl ether represented by formula (XVI) with about two equivalents of a compound represented by formula (XVII), in the presence of an acid in a non-alcoholic organic solvent:

(XVI)

(XVII)

In formulae (XVI) and (XVII), X is selected from the group consisting of —$CH_2CH_2$—, —$CH_2CH_2CH_2CH_2$—, —$CH_2CH_2OCH_2CH_2$—, and —$CH_2CH_2OCH_2CH_2$—; Z is selected from the group consisting of $C(O)OR^1$, $C(O)SR^1$, and $C(O)NR^1R^2$; $R^1$ and $R^2$ are each individually selected from the group consisting of hydrogen, $C_1$ to $C_{20}$ alkyl, and $C_6$-$C_{10}$ aryl; M is a protecting group selected from the group consisting of 9-fluorenylmethyl carbamate, activated amide, and cyclic imide; R is methyl or hydrogen; and n is 1 or 2.

Figure 8A:
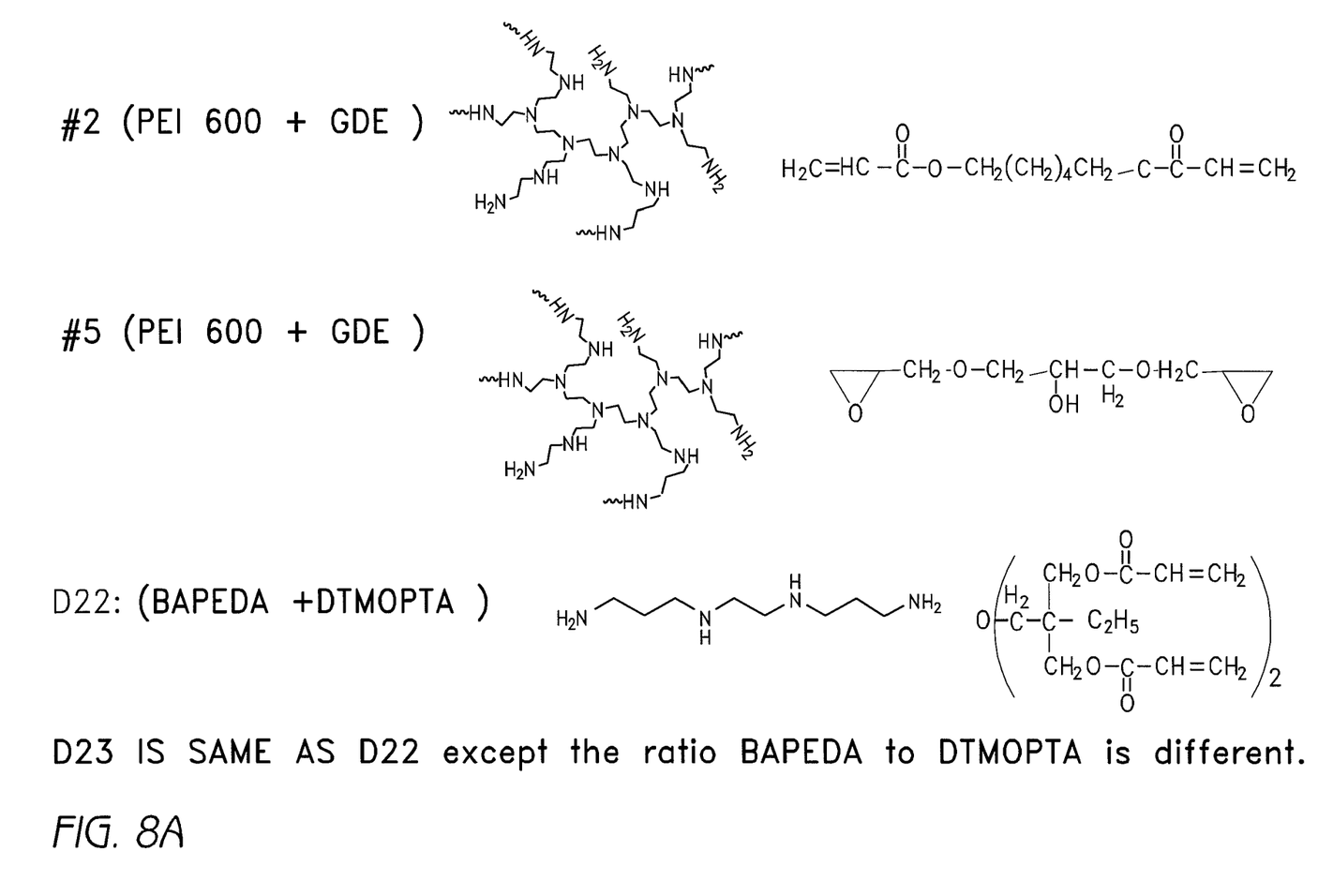
FIGS. 8A & B shows the structures of the polycation compounds used in Example 5 and FIGS. 5A-G
Figure 8B:
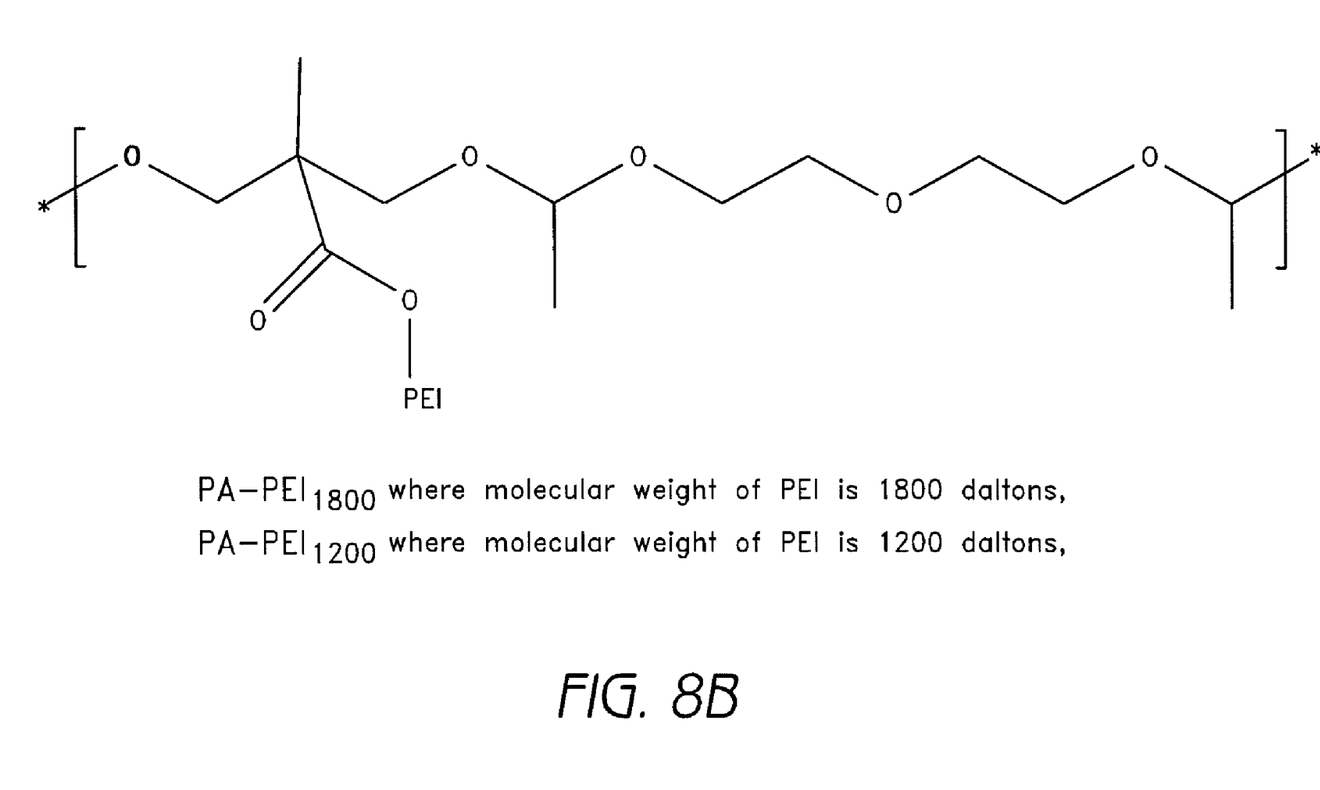

Transportation reagents also include polycationic or cationic lipid based carriers, polycationic or cationic polymer based carriers, polycationic or cationic lipid-polymer based carriers, polycationic or cationic polysaccharide based carriers, and polycationic or cationic protein or peptide based carriers. The transportation reagent may be a dendrimer. The transportation reagent may be a combination of two or more of the compounds listed above. The two or more compounds may be covalently linked (see e.g. PA-PEI in FIG. 8) or may be used as a mixture of two or more compounds (see e.g. D22 and D23 in FIG. 8). Some additional specific examples include SuperFect®, a commercially available activated dendrimer-based transfection agent (QIAGEN®),and jetPEI™ (Qbiogene) which is a linear polyethyleneimine derivative. Additional specific examples are shown in FIG. 8. The examples are illustrative only and are in no way intended to limit the scope of the invention.

In some embodiments, transportation reagents are used to treat the recipient cells prior to transport of the heterologous compound into the cell. However, one of the novel features of the invention is that treatment of the cells with a transportation agent is sufficient to allow intracellular transport of polypeptides and other heterologous compounds into the recipient cell.

Embodiments of the invention are applicable to all cell types, but particularly to eukaryotic cells, more particularly mammalian cells.

We conducted a series of experiments to demonstrate the degree of inhibition of peptide cellular deliver by cationic polymers. Unexpectedly, we found that peptide delivery was enhanced rather than inhibited in the presence of cationic polymers. Specifically, jet-PEI (Qbiogene) and SuperFect (QIAGEN), as illustrated in the examples to follow, enhanced peptide delivery mediated by biotin-labeled Tat peptide. In further experiments, we found unexpectedly that treatment of the cells with a polycationic polymer was sufficient to allow peptide delivery into cells. A peptide which was not a transporter, biotin-RWPSCQKKF (SEQ ID NO: 3), was successfully transported into HeLa cells which had been treated with jet-PEI or SuperFect. Biotin-RWPSCQKKF (SEQ ID NO: 3) alone did not show any transduction confirming that the polycationic polymer was responsible for the transportation of the peptide into the cell. Peptide transport was also shown for human fibroblast cells. We have discovered that pre-treatment of recipient cells with cationic peptides or polymers can provide efficient delivery of peptides and/or proteins into cells.

Preferred embodiments of the invention are directed to improved methods of peptide delivery into cells which include the step of pre-treating cells of interest with a cationic polymer or peptide. By practice of preferred embodiments of the invention, it is unnecessary to perform any covalent binding reaction between the transportation agent and the heterologous compound to be transported. It is also not necessary to make a mixture in advance for peptide delivery into mammalian cells. Peptide delivery is dramatically simplified for cells in vitro and in vivo.

EXAMPLES

Example 1

Figure 1A:
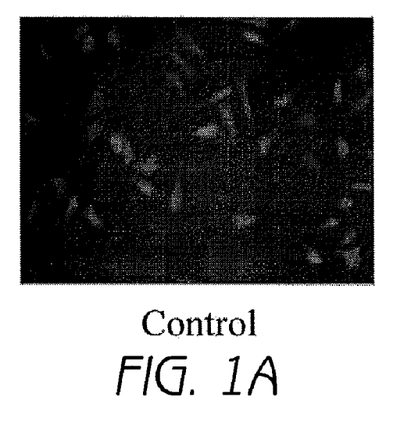
FIG. 1A shows untreated HeLa cells.
Figure 1B:
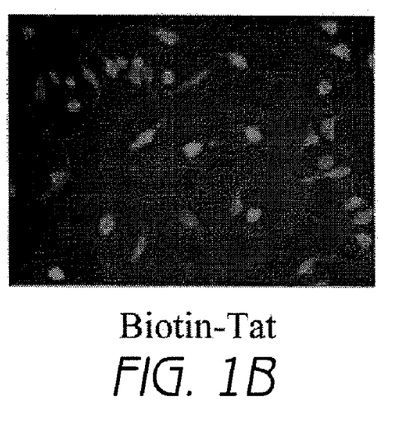
FIG. 1B shows HeLa cells after incubation with biotin-Tat.
Figure 1C:
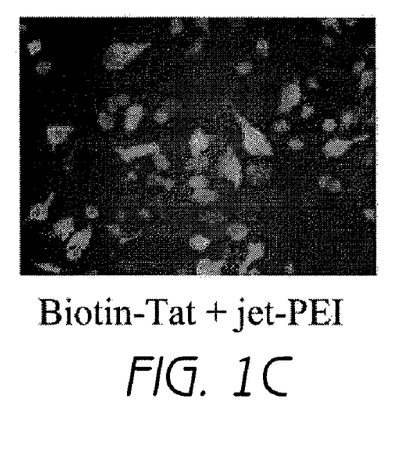
FIG. 1C shows the effect of jet-PEI on the transport of Biotin-Tat into HeLa cells.
Figure 1D:
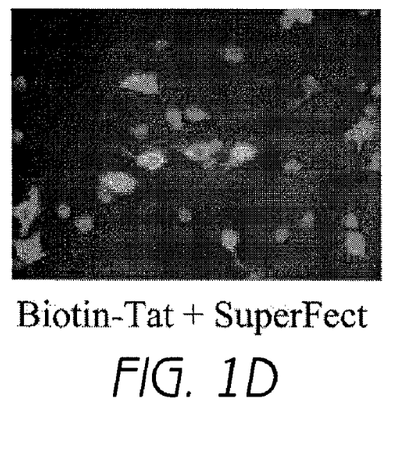
FIG. 1D shows the effect of SuperFect on the transport of Biotin-Tat into HeLa cells.
Figure 2A:
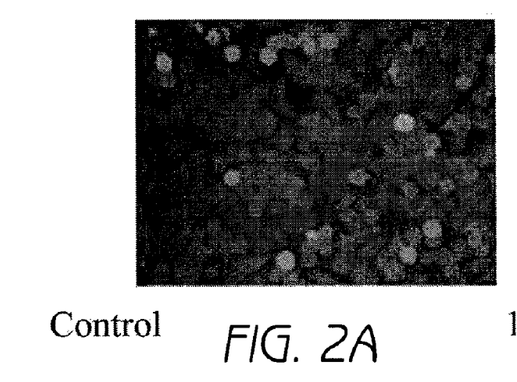
FIG. 2A shows the control which is untreated HeLa cells.
Figure 2B:
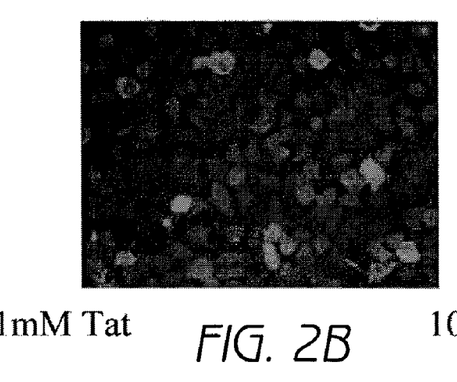
FIG. 2B and 2C show the effect of 1 mM and 10 mM Tat on peptide transport.
Figure 2C:
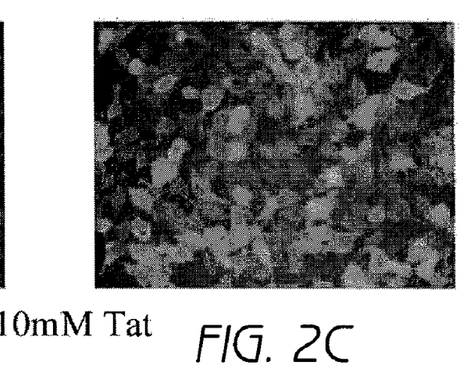
Figure 2D:
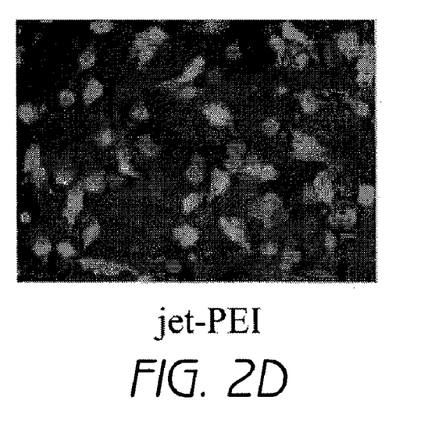
FIGS. 2D and 2E show the effect of jet-PEI and SuperFect on the transport of Biotin-Tat into HeLa cells.
Figure 2E:
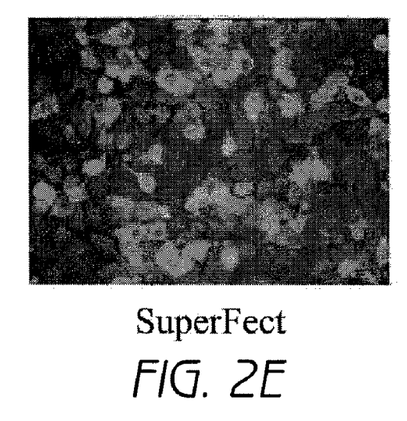

HeLa cells (human cervical carcinoma cell) in 96-well plate were seeded at 24 hours before peptide delivery. Before the delivery, the medium was discarded and the cells were washed twice with PBS. The transportation agent (jetPEI or SuperFect) in PBS was added to HeLa cells and incubated for 60 min. at 37° C. After being washed with PBS, the pretreated cells were then incubated with the cargo Biotin-Tat (Biotin-GRKKRRQRRRPPQC (SEQ ID NO: 2), 10 µM) in PBS for 90 min. at 37° C. Then the cells were washed with PBS and fixed with 0.2% glutaraldehyde / PBS for 5 min at room temperature. After being washed with PBS, cells were treated with 10% methanol for 10 min at room temperature. The cells were washed with PBS again and incubated in DMEM medium at 37° C. for 30min. The cells were washed with PBS again and incubated with streptavidin-FITC at 37° C. for 30min. The cells were washed again and the signal was observed under a fluorescent microscope. Results are shown in FIGS. 1A-D. By streptavidin-FITC, biotin allowed for microscopic visualization of the transported peptide in the HeLa cells. FIGS. 1C and 1D show the enhancement of transport when the cells have been pretreated with either jet-PEI or SuperFect.

Example 2

The transportation agent (Tat (GRKKRRQRRRPPQC (SEQ ID NO: 2), 1 mM or 10 mM), jetPEI or SuperFect) was added to HeLa cells and incubated for 30 min. at 37° C. After being washed with PBS, the pretreated cells were then incubated with the cargo Biotin-Tat (Biotin-GRKKRRQRRRP-PQC (SEQ ID NO: 2), 30 µM) for 10 min. at 37° C. Results are shown in FIGS. 2A-E. In this example, Biotin-Tat was used as a cargo and Tat as a transportation agent in FIGS. 2B and 2C.

Example 3

Figure 3A:
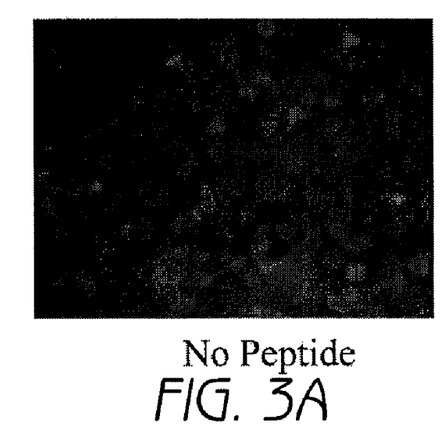
FIGS. 3A shows untreated control cells without peptide and polycation.
Figure 3B:
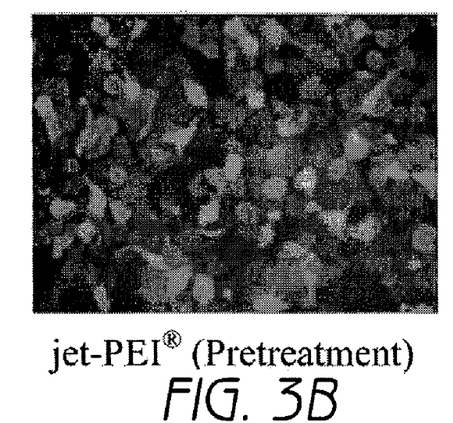
FIG. 3 shows peptide transport into HeLa cells either pretreated (FIGS. 3B and 3E) or simultaneously treated (FIGS. 3C and 3F) with either jet-PEI (FIGS. 3B and 3C) or SuperFect (FIGS. 3E and 3F).

For the pretreatment, the transportation agent (jetPEI or SuperFect) was added to HeLa cells and incubated for 30 min. at 37° C. After being washed with PBS, the pretreated cells were then incubated with the cargo Biotin-RWPSCQKKF (SEQ ID NO: 3) (1 mM) for 10 min. at 37° C. Results are shown in FIGS. 3B and 3E.

For the simultaneous treatment, both the transportation agent (jetPEI or SuperFect) and the cargo Biotin-RWPSC-QKKF (SEQ ID NO: 3) were mixed in a tube for 30 min. at 37° C. After that, the mixture was added to HeLa cells and incubated for 10 min. at 37° C. Results are shown in FIGS. 3C and 3F.

Figure 3C:
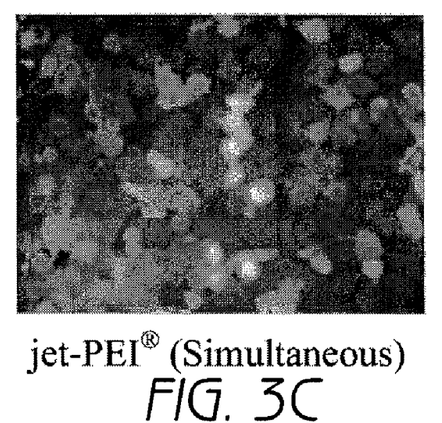
Figure 3D:
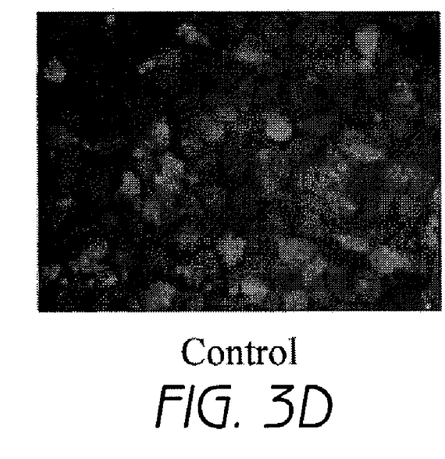
FIG. 3D shows a control treatment with no cell treatment.
Figure 3E:
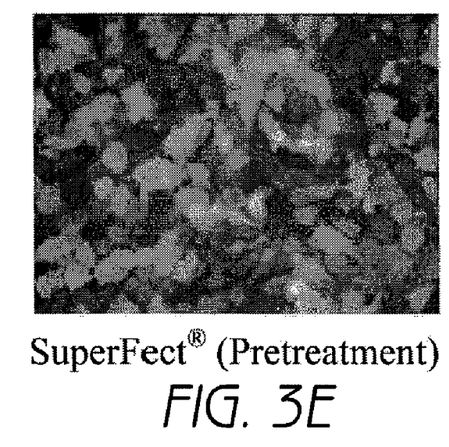
Figure 3F:
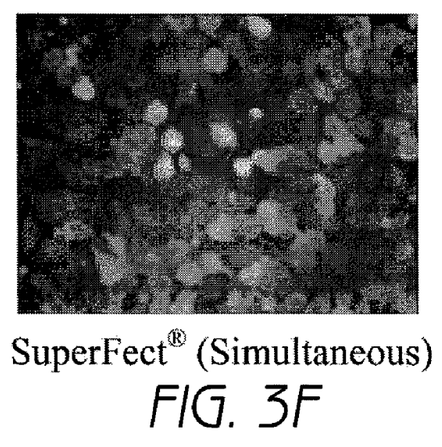
Figure 4A:
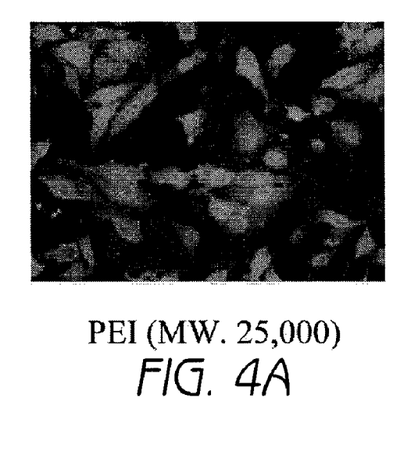
FIG. 4 shows peptide transport into HeLa cells using PEI compounds of various molecular weight as transportation agents. PEI of molecular weights 25,000 (FIG. 4A), 10,000 (FIG. 4B), 1,800 (FIG. 4C), 1,200 (FIG. 4D), and 600 (FIG. 4E) were tested.
Figure 4B:
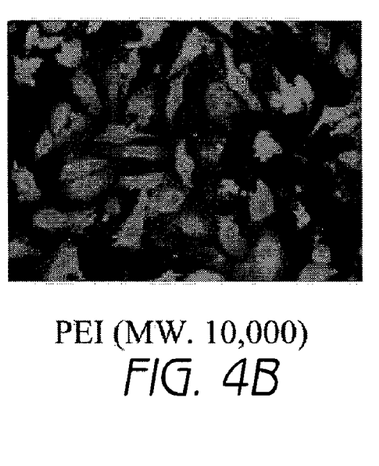
Figure 4C:
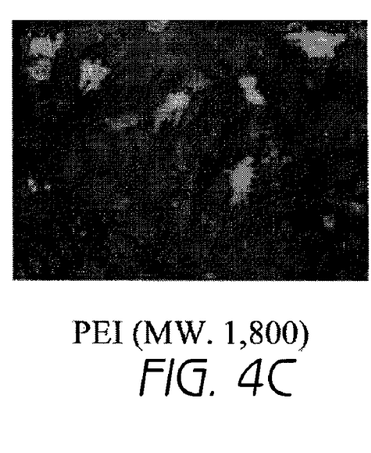
Figure 4D:
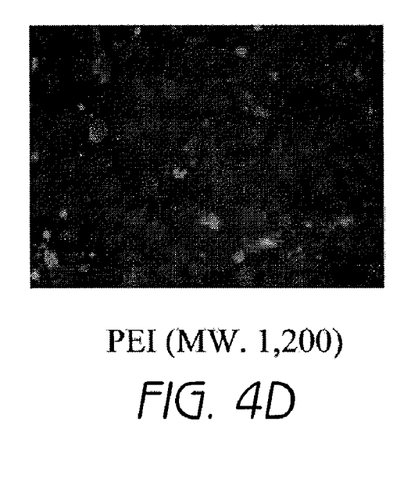
Figure 4E:
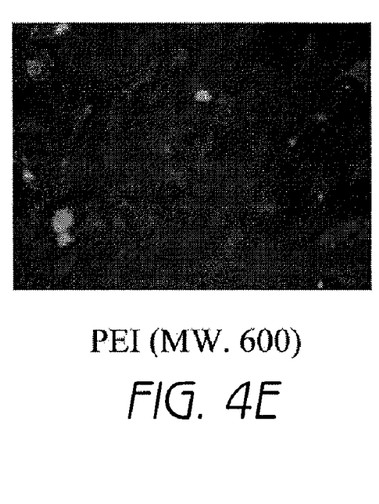
Figure 4F:
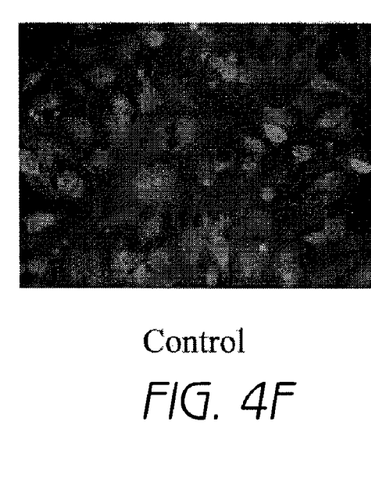
FIG. 4F shows the control (no pretreatment of the cells).
Figure 5A:
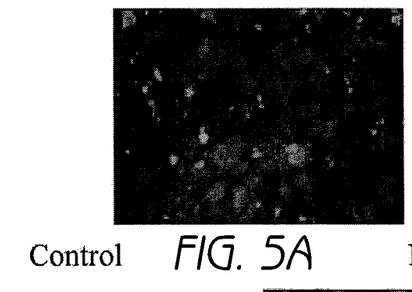
FIG. 5A shows a control treatment with no cell pretreatment.
Figures 5B, 5C:
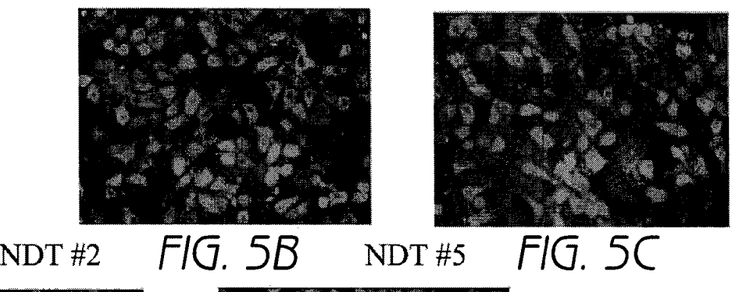
FIG. 5B shows PEI 600+ GDE (see FIG. 8 for structures).
FIG. 5C shows PEI600+ GDE.
Figure 5D:
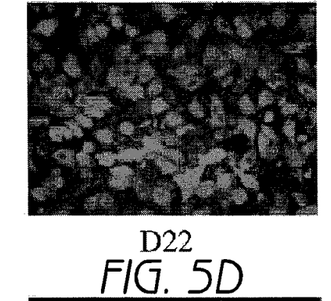
FIGS. 5D and 5E show BAPEDA+DTMOPTA (see FIG. 8 for structures) used in two different ratios.
Figure 5E:
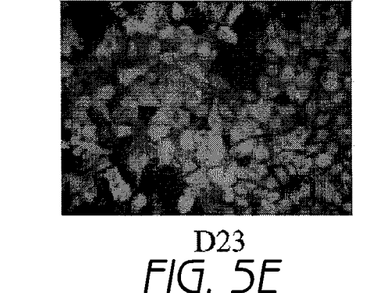
Figure 5F:
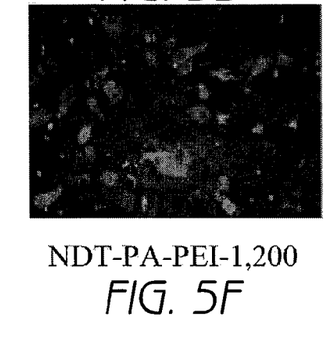
FIG. 5F shows polyacetal-PEI1200.
Figure 5G:
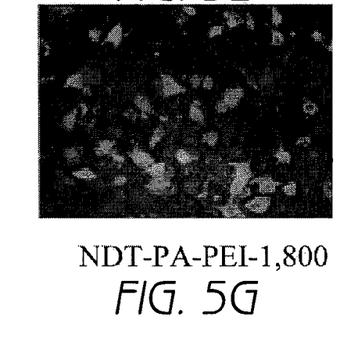
FIG. 5G shows polyacetal-PEI1800. See FIG. 8 for structures of polycations.
Figure 6A:
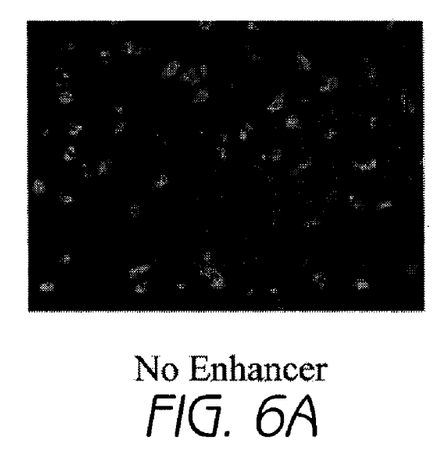
FIG. 6A shows peptide transport in the absence of the transportation agent.
Figure 6B:
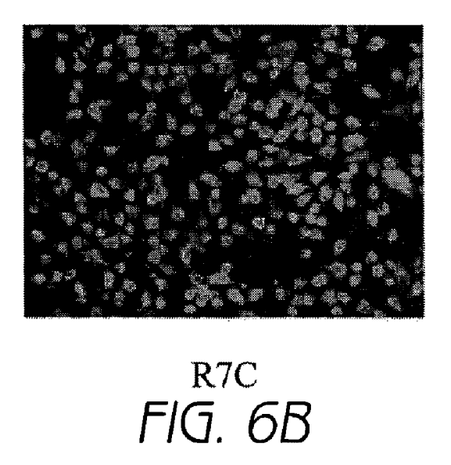
FIG. 6 shows the effect of the transportation agents R7C (RRRRRRRC) (SEQ ID NO: 1) (FIG. 6B), jet-PEI (FIG. 6C), and SuperFect (FIG. 6D) on transport of a peptide (Biotin-RWPSCQKKF) into HT1080 cells (human fibroblast cell).
Figure 6C:
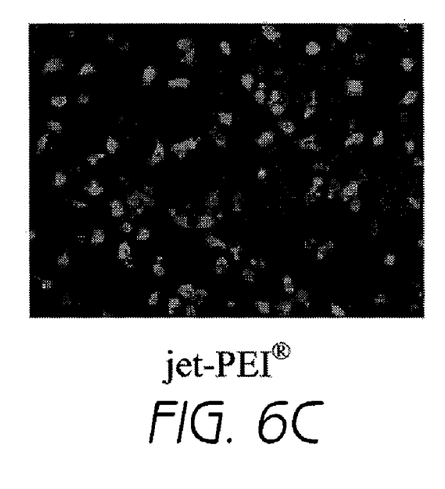
Figure 6D:
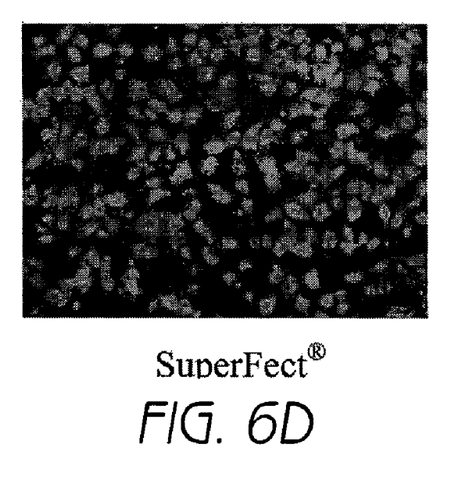
Figure 7A:
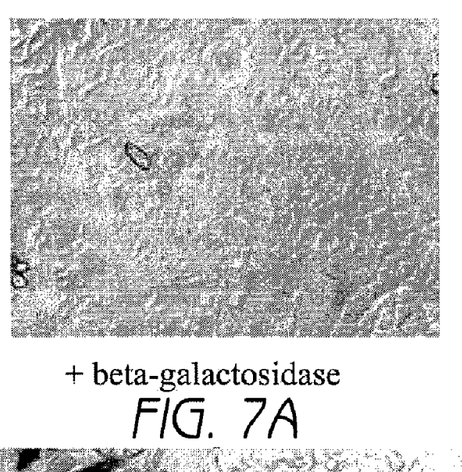
FIG. 7A shows transport of β-galactosidase without a transportation agent.
Figure 7B:
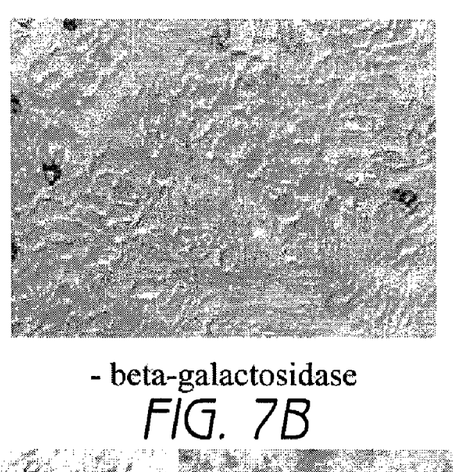
FIG. 7B is a negative control with no added cargo.
Figure 7C:
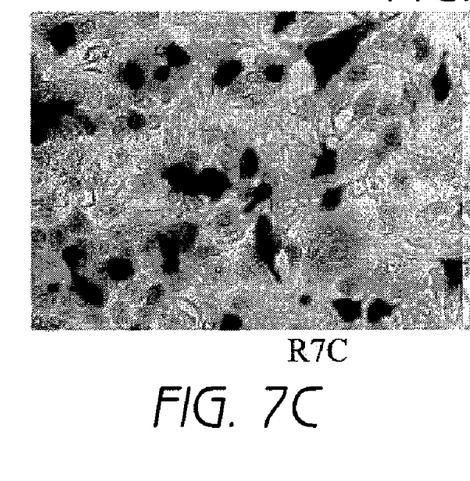
Figure 7D:
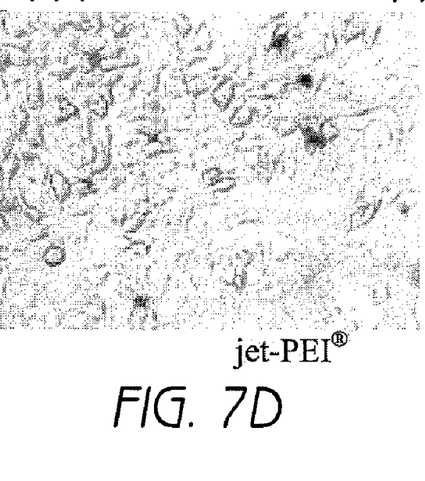
Figure 7E:
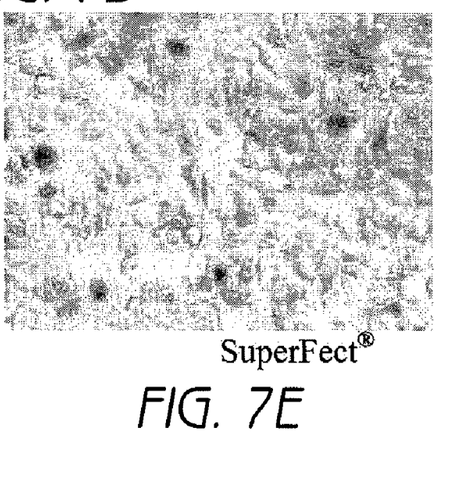

Delivery of the peptide was facilitated by the transportation agent used as a cell pretreatment (FIGS. 3B and 3E) or simultaneously (FIGS. 3C and 3F). FIGS. 3A shows untreated control cells without peptide and polycation. FIGS. 3D shows a control treatment with no cell treatment.

Example 4

In this example, PEI compounds of varying molecular weights (PEI (MW.25,000), PEI (MW.10,000), PEI (MW.1,800), PEI (MW.1,200), PEI (MW.600)) were used as transportation agents for transport into HeLa cells. The cells were pretreated for 30 min. at 37° C. The cargo was Biotin-RWPSCQKKF (SEQ ID NO: 3) (1 mM). After being washed with PBS, incubation of the treated cells with the cargo was for 10 minutes at 37° C. As in Example 3, a carrier such as TAT was not required for efficient peptide delivery.

Example 5

Proprietary cationic polymers were tested for their effect upon the transport of Biotin-RWPSCQKKF (1 mM) into HeLa cells. The cationic polymers (PEI 600+GDE, PEI600+GDE, BAPEDA+DTMOPTA, PA-PEI-1,200, & PA-PEI-1,800, see FIG. 8 for structures) were incubated with HeLa cells for 30 min. at 37° C. After being washed with PBS, incubation of the cells with the Biotin-peptide was for 10 min. at 37° C. The results are shown in FIGS. 5A-G. Structures of the cationic polymers used in this example are shown in FIG. 8.

As in Examples 3-4, a carrier such as TAT was not required for efficient peptide delivery.

Example 6

Example 6 shows the effect of pretreatment of HT 1080 cells (human fibroblast cell) with various transportation agents including poly-arginine (R7C, RRRRRRRC (SEQ ID NO: 1)), jet-PEI® (Qbiogene) and SuperFect® (Qiagen). Pretreatment of the cells was performed at 37° C for 30 min. After being washed with PBS, incubation of the treated cells with the cargo (Biotin-RWPSCQKKF (SEQ ID NO: 3) (1 mM)) was for 10 min. at 37° C. The results are shown in FIGS. 6A-D.

Example 6 shows the general applicability of the described method for other cell types. As in Examples 3-5, a carrier such as TAT was not required for efficient peptide delivery.

Example 7

Example 7 shows the transport of the β-galactosidase protein into HeLa cells using poly-arginine R7C (RRRRRRRC (SEQ ID NO:1)), jet-PEI® (Qbiogene) and SuperFect® (Qiagen) as transportation agents. Briefly, β-galactosidase was dissolved in PBS at 500 nM. HeLa cells in 96-well plate were seeded at 24 hours before peptide delivery. Before the delivery, the medium was discarded and the cells were washed twice with PBS. The transportation agents were added into each well and incubated at 37° C. for 30 min. After being washed twice with PBS, β-galactosidase (500 nM) in PBS was added into each well and incubated at 37° C. for 30 min. Then the cells were washed twice with PBS and fixed with 2% formaldehyde, 0.2% glutaraldehyde in PBS for 5 min at room temperature. After being washed twice with PBS, cells were incubated with X-gal staining solution (1 mg/mL X-gal, 5 mM potassium ferricyanide, 5 mM potassium ferrocyanide, 2 mM $MgCl_2$ in PBS) at 37° C. for 3 hours. The cells were washed twice with PBS and the signal was observed under microscope. The results are shown in FIGS. 7A-E.

This example shows that the described method may be used with proteins as well as peptides. As in Examples 3-6, a carrier such as TAT was not required for efficient peptide delivery.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of transporting a peptide into an isolated mammalian cell comprising: pretreating the isolated mammalian cell with a composition comprising at least one compound comprising a recurring unit represented by a formula selected from the group consisting of formula (I) and (II); administering the peptide to the pretreated cell, and transporting the peptide into the pretreated mammalian cell, wherein the peptide has 2 to 50 amino acids and wherein formula (I) and (II) are represented by:

wherein A comprises at least one acetal group;
wherein B is selected from the group consisting of
—CH—, —CH(CH$_3$)—, CH$_2$ CH—, CH$_2$ C(CH$_3$)—, —CH(CH$_3$)CH—, and —CHCH(CH$_3$)CH(CH$_3$)—;
wherein Z is selected from the group consisting of C(O)OR$^1$, C(O)SR$^1$, C(O)NR$^1$ R$^2$, and VU;
wherein V is a linker group; wherein U is selected from the group consisting of poly(ethyleneimine) (PU), poly(propyleneimine) (PPI), poly(lysine), PAMAM dendrimer, octaamine dendrimer, hexadecaamine dendrimer, enhancer, and targeting receptor;
wherein R$^1$ and R$^2$ are each individually selected from the group consisting of hydrogen, C$_1$ to C$_{10}$ alkyl, and C$_6$ to C$_{10}$ aryl;
wherein D is a linkage selected from the group consisting of carboxylic amide, carboxylic ester, urea, and urethane; and
wherein G is selected from the group consisting of C$_4$ to C$_{20}$ alkyl, C$_6$-C$_{10}$ aryl, and —(OCH$_2$CH$_2$)$_n$—, where n is in the range of 1 to about 250.

2. The method of claim 1, wherein U is poly(ethyleneimine).

3. The method of claim 2 in which the poly(ethyleneimine) has a molecular weight in the range of about 200 to about 100,000 Daltons.

4. The method of claim 2 in which V is —C(O)NH—.

5. The method of claim 1, wherein the cell is an oocyte.

6. The method of claim 1 in which U is poly(lysine).

7. The method of claim 6 in which the poly(lysine) has a molecular weight in the range of about 200 to about 50,000 Daltons.

8. The method of claim 1 in which Z is VU.

9. The method of claim 1, wherein U is selected from the group consisting of polyethyleneimine, enhancer and targeting receptor.

10. The method of claim 9 in which U is a poly(ethylenimine) having a molecular weight in the range of about 200 to about 100,000 Daltons.

11. The method of claim 9 in which U is an enhancer selected from the group consisting of lipid, cholesterol, lipoprotein, fatty acid, lysosomotrophic agent, and fusogenic agent.

12. The method of claim 9 in which U is a targeting receptor selected from the group consisting of transferrin, antibody, antibody fragment, galactose, and mannose.

* * * * *

UNITED STATES PATENT AND TRADEMARK OFFICE
CERTIFICATE OF CORRECTION

PATENT NO. : 7,521,415 B2 Page 1 of 1
APPLICATION NO. : 11/251956
DATED : April 21, 2009
INVENTOR(S) : Minomi et al.

It is certified that error appears in the above-identified patent and that said Letters Patent is hereby corrected as shown below:

Title Page 1, Column 2, Line 25, "Retriefed from the" should be changed to --Retrieved from the--

Column 1, Line 48, "C. Pemelle" should be changed to --C. Pernelle--

Column 4, Line 14, "FIGS. 5A-G" should be changed to --FIGS. 5A-G.--

Column 7, Line 18, "$CH_2CH$—," should be changed to -- —$CH_2CH$—,--

Column 9, Line 52, "and $R_8$ are each" should be changed to --and $R^8$ are each--

Column 9, Line 58, "Z is prefereably" should be changed to --Z is preferably--

Column 11, Line 31, "—$CH_2CH_2OCH_2CH_2$—;" should be changed to

-- —$CH_2CH_2OCH_2CH_2OCH_2CH_2$—;--

Column 15, Line 47, "—CH—, —$CH(CH_3)$—, $CH_2CH$—, $CH_2C(CH_3)$—," should be changed to -- —CH—, —$CH(CH_3)$—, $CH_2CH$—, —$CH_2C(CH_3)$—, --

Column 15, Line 52, "(PU), poly" should be changed to --(PEI), poly--

Signed and Sealed this

Twenty-second Day of September, 2009

David J. Kappos
*Director of the United States Patent and Trademark Office*

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Chemically synthesized

<400> SEQUENCE: 1

Arg Arg Arg Arg Arg Arg Arg Cys
1               5
```

```
<210> SEQ ID NO 2
<211> LENGTH: 14
<212> TYPE: PRT
<213> ORGANISM: Artificial Sequence
<220> FEATURE:
<223> OTHER INFORMATION: Chemically synthesized

<400> SEQUENCE: 2

Gly Arg Lys Lys Arg Arg Gln Arg Arg Arg Pro Pro Gln Cys
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Chemically synthesized

<400> SEQUENCE: 3

Arg Trp Pro Ser Cys Gln Lys Lys Phe
1               5
```